US005494679A

United States Patent [19]
Sage, Jr. et al.

[11] Patent Number: 5,494,679
[45] Date of Patent: Feb. 27, 1996

[54] MOLECULES FOR IONTOPHORETIC DELIVERY

[75] Inventors: Burton H. Sage, Jr., Raleigh; Randal A. Hoke, Cary, both of N.C.

[73] Assignee: Becton Dickinson and Company, Franklin Lakes, N.J.

[21] Appl. No.: 174,589

[22] Filed: Dec. 28, 1993

Related U.S. Application Data

[63] Continuation of Ser. No. 823,730, Jan. 22, 1992, abandoned.
[51] Int. Cl.⁶ .................................................. A61F 13/00
[52] U.S. Cl. .......................... 424/443; 424/447; 604/20; 607/152
[58] Field of Search ............................. 424/443, 497; 604/20; 607/152

[56] References Cited

U.S. PATENT DOCUMENTS

| | | | |
|---|---|---|---|
| 4,585,652 | 4/1986 | Miller et al. | 424/449 |
| 4,878,892 | 11/1989 | Sabalis | 604/20 |
| 4,940,456 | 7/1990 | Sibalis | 604/20 |
| 5,037,643 | 8/1991 | Green | 424/70 |
| 5,042,975 | 8/1991 | Chien | 604/20 |
| 5,250,022 | 10/1993 | Chien | 604/20 |
| 5,250,023 | 10/1993 | Lee | 604/20 |

OTHER PUBLICATIONS

Y. W. Chien, *Annals New York Academy of Sciences* 507:33 (1987).
L. Sanders, *European Journal of Drug Metabolism and Pharmacokinetics* 15:95 (1990).
R. Langer, *Science* 249:1527 (1990).
A. K. Banga et al., *International Journal of Pharmaceutics* 48:15 (1988).
A. K. Banga et al., *Journal of Controlled Release* 7:1 (1988).
B. Meyer et al., *American Journal of the Med. Sciences* 297:321 (1989).
F. Lelawongs et al., *Int'l. Journal of Pharmaceutics* 61:179 (1990).
R. Stephen et al., *Biomed. Biochem. Acta.* 43:553 (1984).
L. Gangarosa et al., *Journal of Pharmaceutical Sciences* 67:1439 (1978).

*Primary Examiner*—D. Gabrielle Phelan
*Attorney, Agent, or Firm*—Susan A. Capello; A. D. Dawson

[57] ABSTRACT

The invention discloses peptides and proteins for iontophoretic delivery. Specifically disclosed are methods for iontophoretic delivery of assemblages of amino acids which comprises modifying said assemblages of amino acids to an isoelectric point less than about 4.0 or greater than about 7.3 with an electrostatic charge of plus or minus 1 and patches with assemblages of amino acids with isoelectric points less than about 4.0 or greater than about 7.3 with an electrostatic charge of plus or minus 1.

18 Claims, 4 Drawing Sheets

MOLECULES FOR IONTOPHORETIC DELIVERY

This application is a continuation of application Ser. No. 07/823,730, filed Jan. 22, 1992, now abandoned.

FIELD OF THE INVENTION

The invention is in the field of peptide and protein drug delivery. In particular, the invention is in the field of iontophoretic peptide and protein drug delivery.

BACKGROUND

The recent developments in molecular biology have provided great amounts of useful peptides and proteins. Not only are previously miniscule amounts of certain peptides and proteins now available in large quantities, but new and modified forms of peptides and proteins are readily available. In conjunction with recent availability, the biological and therapeutic importance of peptides and proteins has enjoyed increased appreciation.

Peptides and proteins are particularly suseptible to degredation when administered by routes other than parenteral. These non-parenteral routes of administration subject the peptides and proteins to gastrointestinal incompatibility (e.g., degradation by proteolytic enzymes) and hepatic "first pass" metabolism in addition to creating varying concentration amounts of the peptide or protein in the blood (i.e., circulating levels). The traditional non-parenteral routes of administration, therefore, are most often ineffective.

Parenteral administration is usually required to achieve therapeutic levels of peptides and proteins. However, peptides and proteins are inherently short acting, thereby requiring frequent injections. The frequent injections subject a patient to additional pain, and potential non-compliance and health hazards.

Alternative means to administer peptide and protein drugs is an active area of research. One notable means for peptide and protein drug delivery is iontophoresis. Iontophoresis refers to the transport of ionic solutes through biological membranes under the influence of an electric field. Iontophoretic drug delivery has the ability to bypass the gastrointestinal and hepatic "first pass" obstacles that render enteral routes of peptide and protein administration of relative little effectiveness.

Iontophoresis, however, has yet to demonstrate widespread success in peptide and protein delivery. However, proteins and peptides appropriate for electrolytic delivery have been described in U.S. Pat. No. 4,940,456 and U.S. Pat. No. 4,878,892 respectively.

However, methods for delivering peptides and proteins by iontophoresis are still cumbersome and require many steps and additions of extraneous materials that are not well suited for simple and efficient iontophoretic delivery. Peptides and proteins for iontophoretic delivery and methods for modifying peptides and proteins for iontophoretic delivery are still mostly unmet.

SUMMARY

The present invention provides peptides and proteins for iontophoretic delivery.

Embodiments of the invention include modified peptides and proteins for iontophoretic delivery.

Other embodiments include methods for delivering peptides and proteins by iontophoresis and patches comprising peptides and proteins for delivery by iontophoresis.

Specific embodiments include the treatment of disease states and afflictions by iontophoretic delivery of peptides and proteins.

The advantages of iontophoretic delivery are many. The invention provides a means for rapid delivery and rapid termination of protein and peptide administration. A peptide or protein with a short activity period is also deliverable by practicing the present invention. The invention also eliminates the potential for overdosing or underdosing a peptide or protein. The problems associated with the "first pass" gastrointestinal and hepatic systems associated with oral administration is also eliminated. And, the risks and inconveniences inherent in parental therapies are avoided. As used in this document, "patient" refers to animals, including humans, household animals such as dogs and cats, livestock such as cattle, horses, sheep, pigs, goats and rabbits, laboratory animals such as mice and rats, and zoo animals such as exotic species. The term "patch", as used in this document, refers to the variety of containment means for drug delivery by iontophoresis in general, as well as specifically for peptides and proteins. Such means include but is not limited to bandages, prefilled passive drug delivery patches, prefilled iontophoretic drug delivery devices, prefilled active drug delivery patches, and reusable iontophoretic drug delivery devices comprising a drug reservoir that is reusable or refillable.

DETAILED DESCRIPTION OF THE INVENTION

The methods and compositions of the invention are not limited to practice with any one particular iontophoretic system or device. Generally, iontophoretic devices comprise at least two electrodes, an electrical energy source (e.g., a battery) and at least one reservoir which contains the protein or polypeptide to be delivered. Several iontophoretic devices are known, such as those disclosed in P. Tyle, *Pharmaceutical Research* 3:318 (1986).

The reservoir or similar structure that contains the peptide or protein to be delivered can be in the form of any material suitable for making contact between the iontophoresis unit and the skin. Suitable materials include, but are not limited to, foams, gels and matrices.

Iontophoresis gels can be karaya gum, other polysaccharide gels, or similar hydrophilic aqueous gels capable of carrying ions. Specific examples of such gels include polyvinyl alcohol, polymethyl pyrollidine, methyl cellulose, polyacrylamide, polyhemas, polyhema derivatives, and the like. The matrix selected should have nonirritating properties to avoid irritating the patients' skin or tissue, suitable conductivity properties to obtain good electrical contact with the skin or tissue, and the ability to act as a carrier medium for the peptides and proteins.

Other means for delivery of peptides and proteins include a patch comprising the peptide or protein as well as reuseable or refillable iontophoretic devices.

Figure 1:
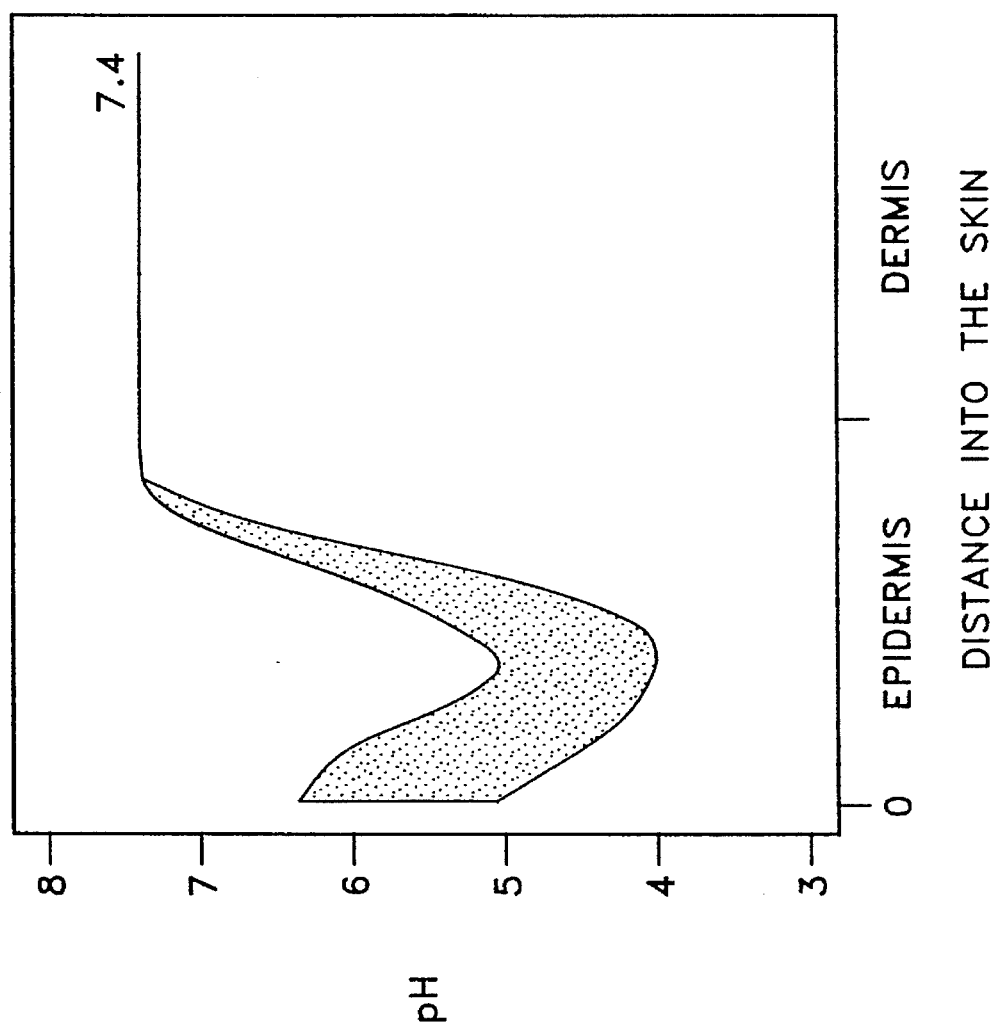
FIG. 1 is a schematic of skin pH versus skin depth.

In passing through the skin, from the outstide stratum corneum to the inside basement membrane, it is well known that the drug molecule will encounter pH's from just below pH5.0 to physiologic pH of 7.3 as shown in FIG. 1 (See e.g. Siddiqui, et al., "Facilitated Transdermal Transport of Insulin" *Journal of Pharmaceutical Sciences* (1987) 76:4 p341). If the isoelectric point is between pH5.0 and pH7.3, at some point during passage to the skin, the molecule will encounter a region where the local pH equals the isoelectric point. At this point, the molecule will have a zero net charge. Since the molecule requires a charge to move during iontophoresis (as distinguished from electrosmosis), at this point the molecule has little mobility due to the electric field and the iontophoresis process is inoperable. Therefore, an isoelectric point outside the range of about pH4.0 to pH7.3 with an electrostatic charge of plus or minus 1 (absolute magnitude of 1) insures that virtually all the molecules will have a net charge, at all locations in the skin, and hence will move due to iontophoresis. An isoelectric point outside about 3–8.3 is preferred.

For example, natural insulin has an isoelectric point of 5.3. If it were placed in a reservoir at pH 7, it would have a negative charge and would move away from negatively charged electrodes. As it moves into the skin, it will reach one of the places where the pH is 5.3. At this point, there will be no force on the molecule from the electric field since the molecule is uncharged. Further, at locations deeper in the skin, the pH can be (FIG. 1) lower. If the molecule diffused to this point, it would become positively charged and hence move back toward the skin surface. At locations less deep in the skin, the pH can be higher. If the molecule diffused to this depth, it would have a negative charge, and now move away from the skin surface. Hence nature has created a situation where the insulin can focus at one depth. Finally, at its isoelectric point the molecule is least soluble. Thus, not only will the molecule be focused at one location, it will tend to precipitate out.

Similarly, if the above insulin molecule were placed in a reservoir at pH 4, it would have a positive charge and would move away from positively charged electrodes. As it moves into the skin, it will reach one of the spots where the pH is 5.3. Again, at this spot the electric field will exert no force on the molecule. Further, at locations deeper in the skin, the pH can be higher. If the molecule diffused to this point, it would become negatively charged and move back toward the surface of the skin due to the electric field. At locations less deep in the skin, the pH can be lower. If the molecule diffuses to this point, it will have a negative charge, and will move away from the surface of the skin due to the electric field. Hence again the molecule will focus at one location. In order to avoid this situation, molecules which are charged at one sign at all locations of the skin are preferred. Means to achieve this are, a) use a native molecule with an isoelectric point outside the pH of the skin or b) use a native molecule with an isoelectric point within the pH range of the skin and modified to obtain an analog with its isoelectric point outside the pH range of skin, i.e., below 4 and above 7.3.

Other characteristics for iontophoretic delivery of peptides and proteins include minimal size. Preferably the molecules should be in the monomer form and have the lowest molecular weight possible. Peptides and proteins have great difficulty penetrating the stratum corneum barrier, which many believe is due to their hydrophilicity, large molecular sizes, and the lipophilic nature of the stratum corneum. If the molecule has a propensity to form polymers and aggegates, this has the effect of multiplying the molecular size by the degree of aggregation. The isoelectric point and molecular size, in combination, increase the degree of mobility that a peptide or protein will have for iontophoretic delivery.

In addition, the peptides and proteins for iontophoretic delivery should preferably have high solubility in water (i.e., low partition coefficient). A peptide or protein with high solubility in water is generally referred to as hydrophilic. It is further preferred that the peptides or proteins of the present invention have a water solubility factor greater than about 1 mg/ml. The peptides and proteins for iontophoretic delivery should preferably have both overall and local hydrophilicity. While overall hydrophilicity implies high water solubility, local hydrophilicity refers to that degree of interaction of portions of the molecule with lipophilic moieties in the skin. High local hydrophilicity implies a low degree of interaction with lipophilic moieties in the skin, increasing the mobility with which the molecule will pass through the skin.

The ability of the peptides and proteins for iontophoretic delivery to maintain bioactivity is also highly desired. While modifications may lead to some loss of activity, as long as the intended result is achieved, loss of some bioactivity is acceptable. Trade-offs between achieving the most efficient deliverable peptide and protein and achieving the most bioactive form of a peptide and protein will result in choosing the peptide or protein with properties closest to achieving the objectives desired.

Assemblages of amino acids refers to the variety of naturally occurring, modified forms of peptides and proteins, and synthetic combinations of amino acid like residues, all of which may have biological activity. All assemblages of amino acids are suitable for use or suitable for modification for iontophoretic delivery in accordance with the present invention. Prodrug forms and other forms where the biological activity remains and its ability to be delivered by iontophoresis is enhanced are also contemplated. Specific examples of suitable peptides and proteins include: Cardio-vascular-active peptides and proteins such as Angiotension II antagonist, Antriopeptins, Bradykinin, and Tissue Plasminogen activator. CNS-active peptides and proteins such as Cholecystokinin (CCK-8 or CCK-32), Delta sleep-inducing peptide (DSIP), β-Endorphin, Melanocyte inhibiting factor-I, Melanocyte stimulating hormone, Neuropeptide Y, and Nerve growth factor. GI-active peptides and proteins such as Gastrin antagonist, Neurotension, Pancreatic enzymes, Somatostatin and its analogs such as octreotide. Immuno-modulating peptides and proteins such as Bursin, Colony stimulating factor, Cyclosporine, Enkephalins, Interferon, Muramyl dipeptide, Thymopoietin, and Tumor necrosis factor. Metabolism-modulating peptides and proteins such as Human growth hormone, Gonadotropins, Insulin, calcitonin and its analogs such as elcatonin, Luteinizing hormone-releasing hormone (LHRH), Oxytocin, Thyrotropin releasing hormone (TRH), Calcitonin gene-related factor, and Vasopressins. Polypeptide growth factors such as Epidermal growth factor (EGF), Insulin-like growth factors I & II (IGF-I & II), Inter-leukin-2 (T-cell growth factor) (Il -2), Nerve growth factor (NGF), Platelet-derived growth factor (PDGF), Transforming growth factor (Type I or δ) (TGF), Cartilage-derived growth factor, Colony-stimulating factors (CSFs), Endothelial-cell growth factors (ECGFs), Erythropoietin, Eye-derived growth factors (EDGF), Fibroblast-derived growth factor (FDGF), Fibroblast growth factors (FGFs), Glial growth factor (GGF), Osteosarcoma-derived growth factor (ODGF), Thymosin, and Transforming growth factor (Type II or β)(TGF).

The ability to modify a peptide or protein to its minimal size is readily achievable. For example, it is known that human growth hormone-releasing factor (hGRF) is a forty-four amino acid long peptide (hGRF(1–44)-NH2)) that displays high potency with the carboxy terminus deleted (hGRF(1–29)-NH2), see A. M. Felix, *Pharmaceutical Technology* May 1991 (page 28). In general, smaller portions of large peptides are available through direct synthesis. These fragments can then be tested for the appropriate bioactivity. Traditionally, fragment peptides are synthesized "one-at-a-time" by automated solid phase synthesis. Recently, however, rapid methods of multiple peptide synthesis have become available which facilitate this process (Houghten, R. A., *Proc. Natl. Acad. Sci.* U.S.A. 82 (1985) 5131.

The isoelectric point (pI) of a bioactive peptide can be adjusted by several methods. One method is to substitute specific undesirable residues for more desirable ones. For instance, to raise the pI of a peptide, one would remove or exchange negatively charged residues such as glutamate or aspartate residues, replacing them with neutral or positively charged residues such as lysine or arginine. Neutral residues such as glycine and proline, can be replaced with positively charged residues such as lysine and arginine. Charged residues could also be conveniently added to the amino or carboxy terminii of the peptide chain by direct solid phase synthesis.

Another method involves developing a pro-drug of the peptide of interest. For instance, negatively charged side chains of aspartic acid, glutamic acid, or the carboxy terminus could be esterified with a neutral or positively charged group which is subsequently removed in vivo, restoring the original peptide structure.

Peptide and protein modifications may be realized by a number of routes. Direct chemical modifications are one possible path (see Lundblad, R. L., Chemical Reagents for Protein Modification, (1991), CRC Press, Boca Raton, Fla.). Site directed mutagenesis of nucleic acids and subsequent expression of the proteins is another route. The use of automated peptide synthesis techniques extends the range of possibilities since un-natural amino acids can be incorporated into the peptide/protein. Modification by the use of enzymes is a fourth method of developing analogues. Enzymes which carry out a range of post-translational modifications are known. Among the protein modifying enzymes are carboxylases, phosphate kinases, hydroxylases and glycosylases. The above modification techniques can be used either alone or in combinations to achieve the desired results in terms of isoelectric point, total charge, and bioactivity.

These methods of adding or altering the charge characteristics of peptides often improve their solubility characteristics as well. Proteins with isoelectric points outside the range of 4 to 7.4 will not likely precipitate or aggregate during transit through the skin.

Means for modifying peptides and proteins to obtain molecules with positive charges through the isoelectric point from about 4 to about 7.4 include sulphation. Sulphated proteins can be prepared by any of several methods described in the literature. Under appropriate conditions, sulfonate groups are specifically appended to aliphatic hydroxyl groups such as are found on serine and threonine residues. Insulin, for example, has been sulfated by treatment with concentrated sulfuric acid, either alone or in conjunction with a dehydrating agent such as carbodiimide (Reitz, H. C., Ferrel, R. E., Fraenkel-Conrat, H., et al (1946) *J. Am Chem. Soc.*, 68, 1024–1031 and Cerami, A., Pongor, S., Brownlee, M. (1985) U.S. Pat. No. 4,534,894). Pyridinium sulfonic acid was also used to introduce sulfate groups to insulin (Sluyterman, L. A. A. E., Kwestroo-Van den Bosch, J. M. (1960) *Biochem. et Biophys. Acta*, 38, 102–113). Such procedures should work on all the native insulins such as human, porcine, and bovine, their synthetic molecules, and analogs thereof.

The following examples illustrate the specific embodiments of the invention described in this document. As would be apparent to skilled artisans, various changes and modifications are possible and are contemplated within the scope of the invention described.

EXAMPLE 1

Preparation of Monomeric Insulin with pI>7

A monomeric insulin such as the des-pentapeptide (B26–30) free acid or amide, is prepared enxymatically using established literature procedures. To this base material is coupled a peptide such as lysyl-lysine, carrying a suitable number of charged groups.

Experimental

Porcine insulin (Calbiochem Corp., La Jolla, Calif.) is cleaved with trypsin to produce the des-octapeptide (B23–30) analogue. This material is coupled with H-Gly-Phe-Phe-NH2 using trypsin assisted catalysis in mixed aqueous-organic systems following established procedures (Nakagawa, S. H., Tager, H. S. (1986) *J. Biol. Chem.*, 261, 7332–7341). The resulting des-pentapeptide (B26–30) insulin is purified by ion exchange chromatography.

The dipeptide N-(Boc)-ε-Boc-lysyl-ε-Boc-lysine is prepared by coupling N-(Boc)-ε-Boc-lysine N-hydroxy succinimide ester with ε-Boc-lysine in anhydrous dimethyl formamide. The reaction is allowed to stir overnight, evaporated in vacuo, and taken up in ethyl acetate. The organic layer is washed with aqueous citric acid, water, and dried. The resulting oil is triturated with hexane to yield a solid product.

The dipeptide is then coupled to des-pentapeptide insulin using an established fragment coupling technique (Kisfaludy, L., Roberts, J. E., Johnson, R. H., et al. (1970) *J. Org. Chem.*, 35, 3563–3565)

The pentafluorophenyl ester of the dipeptide is prepared in situ by treatment with one equivalent of the dicyclohexylcarbodiimide-pentafluorophenol "complex" in dimethylformamide at 0 C. The reaction is allowed to warm slowly to room temperature over a period of 1 hour. The solution is filtered to remove the precipitated dicyclohexyl urea, and added to a solution of insulin in dimethylformamide. The activated dipeptide is added in a 10-fold molar excess. The reaction is stirred for 4 hours at room temperature, at which time diethyl ether is added to precipitate the protein. The precipitate is recovered by centrifugation and treated for 1 hour with anhydrous trifluoroacetic acid to remove the Boc protecting groups. Following removal of the acid in vacuo, the product is purified by ion exchange chromatography on sulfonated sepharose in 20% acetic acid, using a sodium chloride gradient to dilute the proteins.

The product of this sequence of reactions is an insulin analogue carrying a lysyl-lysine dipeptide appended to the N-terminal positions of the A and B chains. The pI of this monomeric analogue is 8.4.

EXAMPLE 2

Lack of Transport of Insulin—pI5.3

The following examples have been taken using the porcine skin flap model (J. Riviere et al., *Fund. Appl. Toxicol.* 7:444 (1986) to study transdermal transport:

Two skin flaps

Duration of iontophoresis 4 hrs at 0.9 ma DC

Cathode dosing solution—regular insulin (Eli Lilly, Indianapolis, Ind.)>100 Units/ml,pI 5.3

Anode solution 10% saline

Area of electrode 4.5 cm$^2$—Porex TM reservoir with Ag mesh anode

Current density 200 µA/cm2

Samples of perfusate taken every 30 minutes starting with one hour prior to iontophoresis until 4 hours after iontophoresis.

Specimens analyzed using insulin RIA—sensitive to 10 µU/ml (400 picograms/ml) (Cambridge Research, Boston, Mass.)

Result—all samples had concentrations of insulin below minimally detectable levels.

EXAMPLE 3

Transport of Sulfated Insulin pI=1.0

Two skin flaps

Duration of iontophoresis—4 hours at 0.9 ma DC

Cathode dosing solution—sulfated insulin (Connought Labs, Toronto, Canada), 100 U/ml,pI—1.0

Anode solution 10% saline

Area of electrode 4.5 cm$^2$—Porex TM reservoir with Ag/AgCl mesh cathode

Current density 200 µA/cm2

Samples of perfusate taken every 30 minutes starting with one hour before iontophoresis until 4 hours after iontophoresis.

Specimens analyzed using insulin RIA (Cambridge Research, Boston, Mass.) sensitive to 10 µU/ml (400 picograms/ml).

Figure 2:
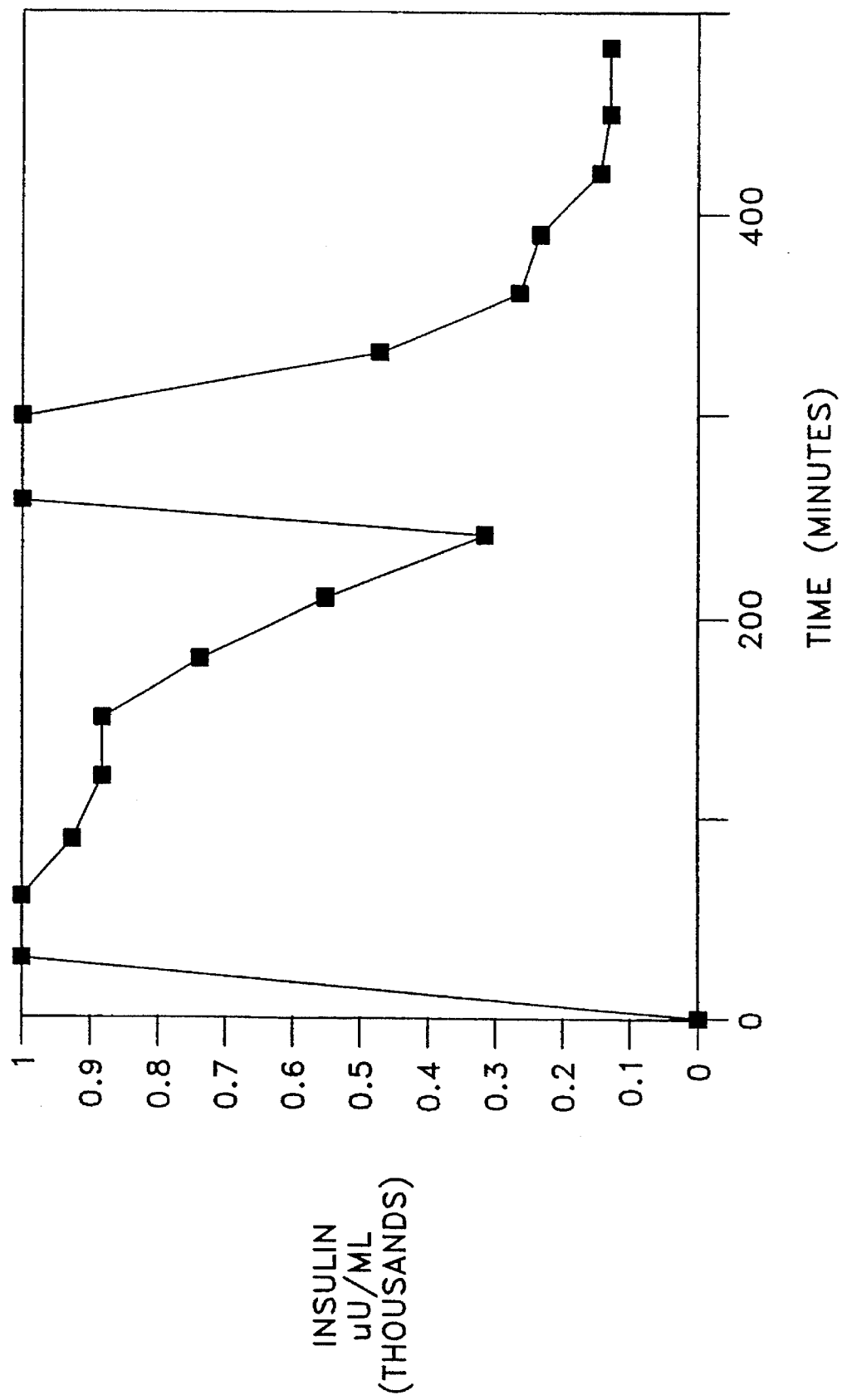
FIG. 2 is a schematic of a skin flap experiment demonstrating iontophoretic delivery of a sulphated insulin.

Result: See FIG. 2—significant transport of insulin analog (sulfated insulin)

EXAMPLE 4

Thyrotropin-releasing hormone (TRH) has a pKa of approximately 6.2. It carries decreasing (positive) charge over the pH range 5–7, being essentially +1 charged at the low pH and progressing toward being uncharged at pH 7. Although delivery of this compound under the influence of an electric field has been documented, the fluxes indicated that the drug was carried passively by convection (Burnette, R. R., et al., J. Pharm. Sci., 75, (1986), 738–743.)

Figure 4:
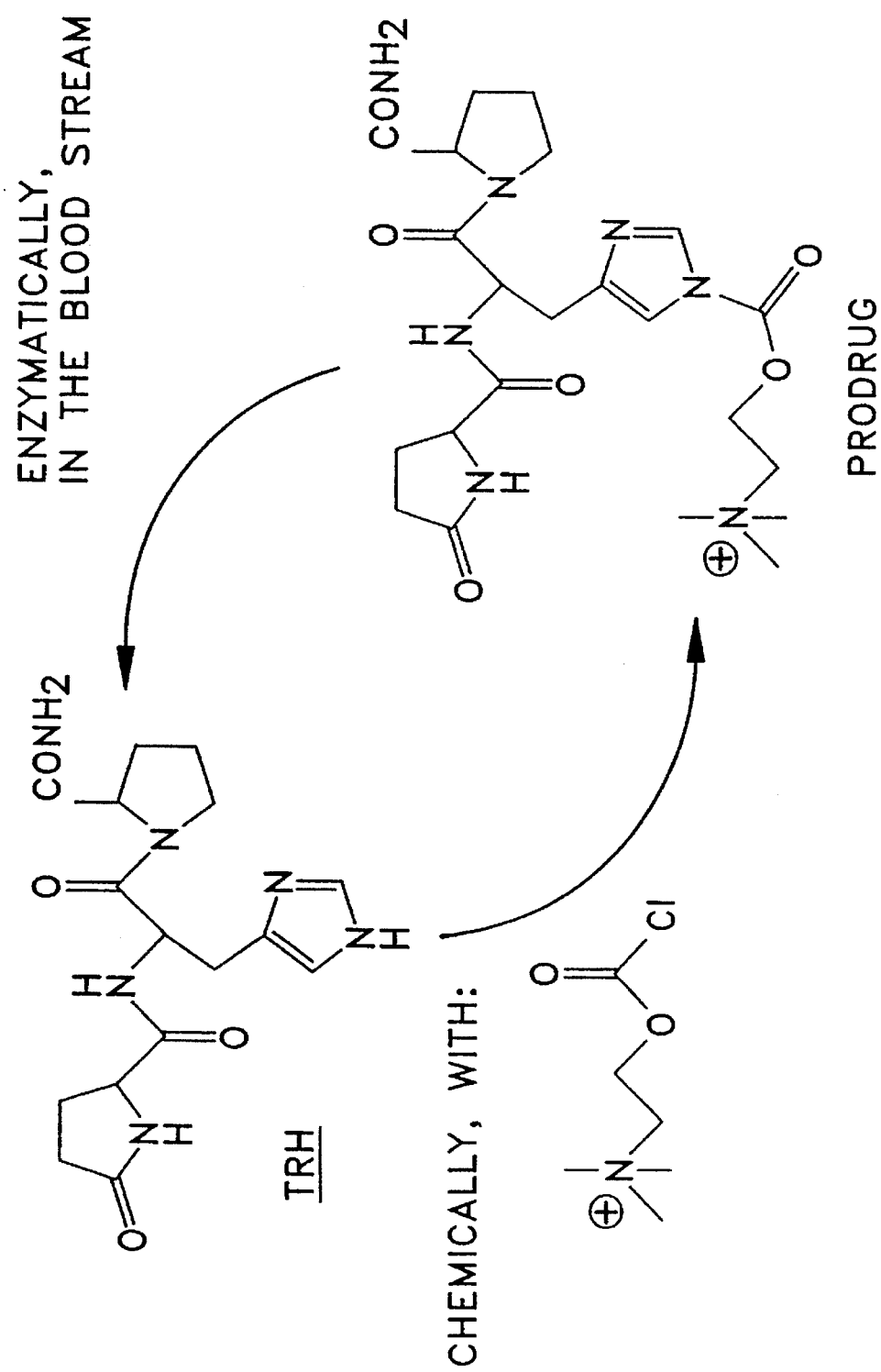
FIG. 4 is a schematic of the formation of an LHRH prodrug.

A prodrug of TRH which carries a positive charge over the pH range of 4–7 can be prepared using the methods of Bundgaard, et al. (Pharm. Res., 7, (1990), 885–892.) In a modification of the method cited, choline chloroformate (formed from choline and phosgene) is substituted for the hydrophobic chloroformates in the synthetic procedure (See FIG. 4). This substitution leads to a TRH prodrug with a quaternary amine functionality which maintains a +1 charge at all pH's. This compound will exhibit high water solubility and will remain charged over the pH range of 4–7.

EXAMPLE 5

Iontophoretic Delivery of LHRH (pI~11) Using the Skin Flap Model of J. Riviere Electrodes—Porex™ sandwich 1 cm$^2$ with Ag anode mesh made by Becton Dickinson Research Center LHRH (Luteinizing hormone releasing hormone) solution: 1 mgm/ML in 154 mM NaCl plus 10 mM MES buffer pH6.0

Indifferent electrode solution: NaCl 159 mgm/ML

Iontophoresis current 0.2 ma for 3 hours

Figure 3:
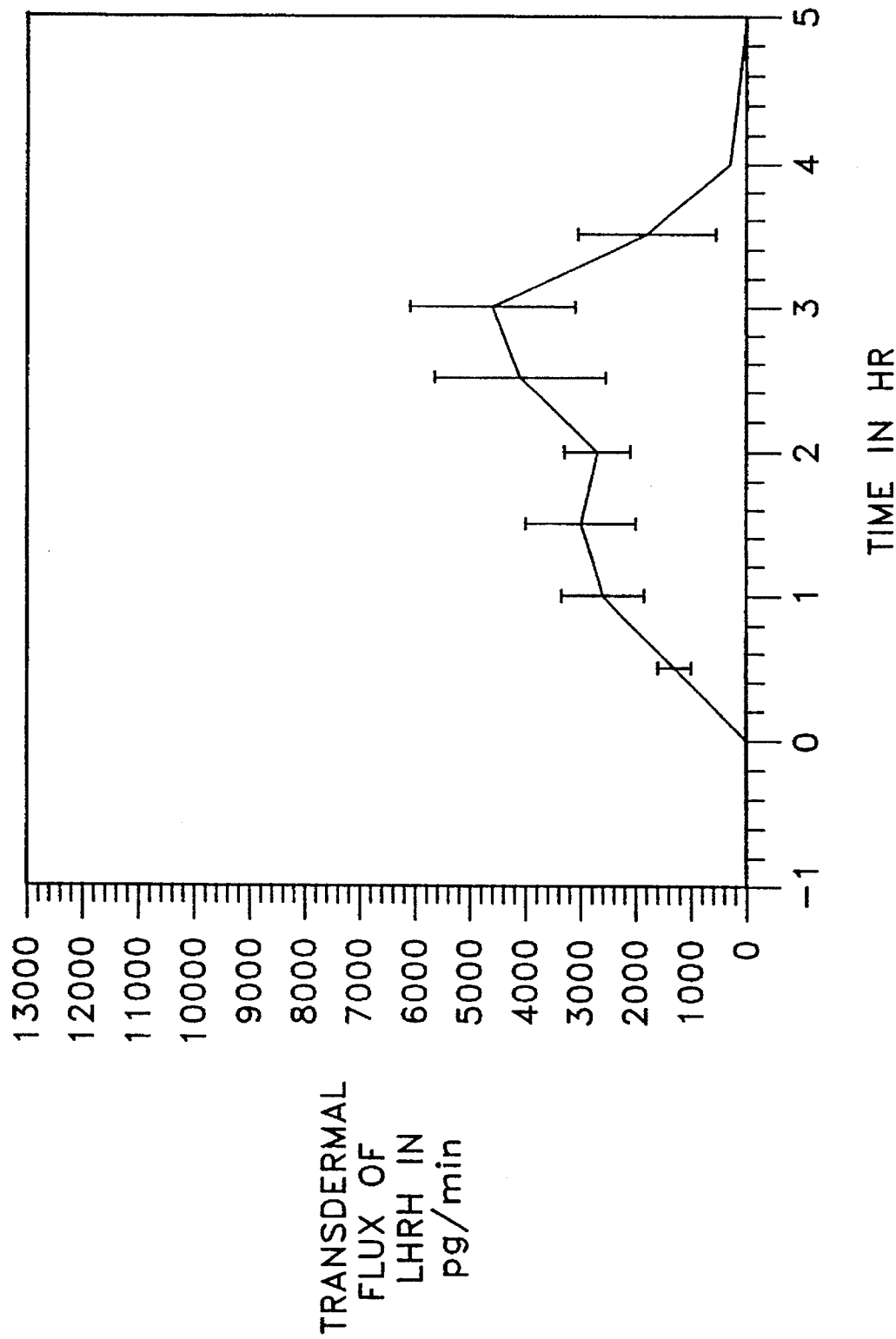
FIG. 3 is a schematic of a skin flap experiment demonstrating iontophoretic delivery of LHRH.

FIG. 3—mean ±ISD for six replicate skin flaps

Source of LHRH: Sigma Chemical Co., St. Louis, Mo.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A method for preparing proteins or peptides for iontophoretic delivery comprising:

modifying said proteins or peptides by chemical modification to an isoelectric point less than about 4.0 or greater than about 7.3 with an electrostatic charge of at least plus or minus 1 over the pH range of about 4.0 to about 7.3.

2. The method of claim 1 in which the isoelectric point is less than about 3.0 or greater than about 8.3.

3. The method of claim 1 in which the peptides or proteins have a water solubility factor greater than about 1 mg/ml.

4. A patch for iontophoretic delivery which comprises proteins and peptides having an isoelectric point of less than about 4.0 or greater than about 7.3 with at least an electrostatic charge of plus or minus 1 over the pH range, of human skin, of about 4.0 to about 7.3.

5. The patch of claim 4 in which the isoelectric point is less than about 3.0 or greater than about 8.3.

6. The patch of claim 4 in which the peptides or proteins have a water solubility factor greater than about 1 mg/ml.

7. The patch of claim 4 in which the peptides or proteins are naturally occurring.

8. The patch of claim 4 in which the peptides or proteins are analogs of naturally occurring peptides or proteins.

9. The patch of claim 8 in which the peptide is elcatonin.

10. The patch of claim 8 in which the peptide is octreotide.

11. The patch of claim 8 in which the peptide is insulin.

12. The patch of claim 8 in which the peptide is LHRH.

13. A method for preparing proteins or peptides for iontophoretic delivery comprising:

modifying said proteins or peptides by amino acid substitution to an isoelectric point less than about 4.0 or greater than about 7.3 with an electrostatic charge of at least plus or minus 1 over the pH range of about 4.0 to about 7.3.

14. The method of claim 13 in which the isoelectric point is less than about 3.0 or greater than about 8.3.

15. The method of claim 13 in which the peptides or proteins have a water solubility factor greater than about 1 mg/ml.

16. A method for preparing proteins or peptides for iontophoretic delivery comprising:

modifying said proteins or peptides by amino acid addition or deletion to an isoelectric point less than about 4.0 or greater than about 7.3 with an electrostatic charge of at least plus or minus 1 over the pH range of about 4.0 to about 7.3.

17. The method of claim 16 in which the isoelectric point is less than about 3.0 or greater than about 8.3.

18. The method of claim 16 in which the peptides or proteins have a water solubility factor greater than about 1 mg/ml.

* * * * *